United States Patent [19]

Agnès et al.

[11] 4,429,147
[45] Jan. 31, 1984

[54] PROCESS FOR THE PREPARATION OF DIESTERS OF SATURATED CARBOXYLIC ACIDS

[75] Inventors: Giovanni Agnès; Guglielmo Rucci; Claudio Santini, all of Novara, Italy

[73] Assignee: Montedison S.p.A., Milan, Italy

[21] Appl. No.: 396,670

[22] Filed: Jul. 9, 1982

[30] Foreign Application Priority Data

Jul. 14, 1981 [IT] Italy ................................ 22918 A/81

[51] Int. Cl.³ .............................................. C07C 67/38
[52] U.S. Cl. ......................................... 560/81; 560/97; 560/204; 502/171; 502/326
[58] Field of Search ......................... 560/81, 97, 204; 252/429 R, 431 R, 431 C, 431 P, 441, 447, 474, 476

[56] References Cited

U.S. PATENT DOCUMENTS

| | | | |
|---|---|---|---|
| 3,397,226 | 8/1968 | Fenton | 560/204 |
| 4,039,572 | 8/1977 | Funakoshi et al. | 560/204 X |
| 4,160,107 | 7/1979 | Agnes et al. | 560/204 |
| 4,234,740 | 11/1980 | Umemura et al. | 560/81 |

FOREIGN PATENT DOCUMENTS 2024821  1/1980  United Kingdom .

*Primary Examiner*—Natalie Trousof
*Assistant Examiner*—Vera C. Clarke
*Attorney, Agent, or Firm*—Morgan, Finnegan, Pine, Foley & Lee

[57] ABSTRACT

Alkyl diesters of saturated dicarboxylic acids are prepared by catalytic reaction of olefinic hydrocarbons with carbon monoxide and alkoxylic copper salts, in the presence of a Palladium catalyst.

The products obtained find useful applications in the field of plasticizers for synthetic resins, in the field of lubricants and of hydraulic fluids, etc.

11 Claims, No Drawings

PROCESS FOR THE PREPARATION OF DIESTERS OF SATURATED CARBOXYLIC ACIDS

BACKGROUND OF THE INVENTION

The following formula (I) can be attributed to the alkyl diesters of saturated dicarboxylic acids obtainable according to the present invention:

wherein $R_1$ and $R_2$ are each selected from the group consisting of hydrogen atoms, $C_1$–$C_6$ alkyl, $C_1$–$C_8$ aryl, alkylaryl and arylalkyl groups and R is a $C_1$–$C_8$ alkyl or an alkoxyethyl —$CH_2$—$CH_2$—OR' group, wherein R' is a $C_1$–$C_6$ alkyl group.

It is known to prepare (di)esters of (di)-carboxylic acids, starting from olefinic compounds, by reacting an olefin with carbon monoxide and an alcohol, in the presence of catalysts.

There are obtained the corresponding esters, diesters and betalkoxy substituted esters, of mono- and dicarboxylic acids; in the first case being unsaturated esters having one carbon atom in excess, in the two latter, being saturated esters, containing two carbon atoms in excess with respect to the starting olefin.

U.S. Pat. No. 3,397,226, for instance, describes a process in which an olefin is made to react with carbon monoxide and an alcohol in the presence of a redox-system consisting of a metal salt catalyst of the platinum group associated with a multi-valency metal salt, such as iron or copper.

Such catalysts system is kept on its higher valency or oxidation level by the addition of molecular oxygen, of halogens, or by other methods, in order to secure for the redox system its effectiveness in a continuous operation, while regenerating the redox salt species on its higher oxydation level.

The reaction, according to a preferred embodiment, is carried out in an essentially anhydrous medium, by also resorting to the use of quantitative portions of dehydrating agents, etc.

The above described redox catalytic system, in fact, is extremely sensitive to the presence of water, which leads to a reduction of the yields in the desired product with a contemporaneous increase of the formation of undesired by-products such as, for instance, $CO_2$, etc.

Moreover, the possible dehydrating agent used therein may not be used again at the end of the reaction because it proves to be degraded. On the whole there arise, thus, considerable burdensome and expensive operational difficulties, bound to the non-selectivity of the reaction (separation of products from the mixtures obtained) and to the purification of the products that must be freed of the by-products that were formed, etc., with considerable prejudice to the economical convenience of the process itself.

Further, the use of gaseous mixes of carbon monoxide and oxygen $CO+O_2$, involves real risks of explosion (explosion hazards), of a practically prohibitive character for a proper operation of the process.

As an alternative for the above said process, there has been suggested that the same reaction be conducted in a gaseous phase, in the presence of a catalyst of the platinum group and of an ester of a nitrous acid and possibly of oxygen.

The process, described in U.K. Pat. Application No. 2,024,821, asserts to obtain better yields and a greater selectivity. Nevertheless, also in this process, the contemporaneous quantitative forming of by-products, makes the problem of separation and purification relatively burdensome with regard to a correct evaluation of the industrial economical convenience.

On the other hand, the presence of oxygen in the cycle may lead to the formation of explosive organical nitrates.

OBJECTS OF THE INVENTION

The present invention relates to a process for the preparation of alkyl diesters of dicarboxylic acids of formula (I). In particular, it relates to a catalytic process for the preparation of alkyl diesters of saturated dicarboxylic acids (I) by reaction of olefinic hydrocarbons with carbon monoxide and alkoxylic copper (II) salts, in the presence of a palladium catalyst.

In this way there are obtained the alkyl diesters of the saturated acids (I) corresponding to the olefinic hydrocarbons used as the starting material, that is, the alkyl diesters of the saturated dicarboxylic acids having 2 carbon atoms in excess with respect to those present in the used olefin.

Thus, by way of example, if the starting olefin is ethylene, according to the process object of this invention, there will be obtained selectively an alkyl diester of the succinic acid.

Other alkyl esters of saturated dicarboxylic acids are correspondingly and respectively obtained by using as the starting reactant a different olefin: from 1-hexene the alkyl-diester of 1.2-hexandicarboxylic acid, the diesters of methyl-succinic and glutaric acids from propylene, etc. From the esters, if desired, the corresponding acid may be obtained according to the conventional techniques of the Art (hydrolysis, etc.).

The acids and esters thus obtained represent important compounds possessing well known and ample applicative possibilities that are of considerable industrial interest.

In fact, said compounds (succinic alkyl diesters) may find an application in the field of plasticizers in various synthetic resins; or they may be used in the field of lubricants and in that of hydraulic fluids, etc.

Polyesters are used, for instance, in polyurethanic foams and in linings.

THE PRESENT INVENTION

Thus, it is an object of the present invention to provide a process for the preparation of alkyl esters (I) of saturated dicarboxylic acids, starting from olefins having two (2) carbon atoms less, which be a simple and economical process and in particular free of the drawbacks specified in and described in the known Art taken into consideration.

The process, object of this invention, in particular is characterized in that there are obtained high yields combined with a high selectivity and purity of the products. The process consist in the reaction of an olefinic compound with carbon monoxide and with an alkoxylic copper salt, in the presence of a palladium catalyst better defined later on.

In the process of this invention, the alkyl esters of the saturated dicarboxylic acids are obtained according to much faster and more economical operational conditions with respect to those described in the previously discussed processes, thereby representing a real technical progress that becomes available to those skilled in the Art.

GENERAL DESCRIPTION OF THE INVENTION

According to this invention, there is provided a process for the preparation of alkyl diesters of saturated dicarboxylic acids of formula (I) as above defined, characterized in that said alkyl diesters of saturated dicarboxylic acids are obtained by reacting an unsaturated olefinic compound of formula (II):

$$R_1CH=CHR_2 \qquad (II)$$

wherein $R_1$ and $R_2$, either equal to or different from each other, are each selected from the group consisting of a hydrogen atom, an alkyl group having up to 6 carbon atoms, or an aryl, an alkylaryl, an arylalkyl group having up to 8 carbon atoms, with a compound of copper (II) of the formula Cu(OR)X, wherein R represents an alkyl radical having from 1 to 8 carbon atoms, preferably from 1 to 4 carbon atoms or an alkoxyethyl radical —$CH_2$—$CH_2$—OR′, wherein R′ is an alkyl having up to 6 carbon atoms, and where X is a halogen atom chosen between chlorine and bromine, but preferably is chlorine, and with carbon monoxide in the presence of at least a palladium salt or a zerovalent palladium compound or of metal palladium, possibly in an inert, substantially anhydrous medium, at a temperature comprised between about 20° C. and 200° C.

The process may be schematically represented by the following equation:

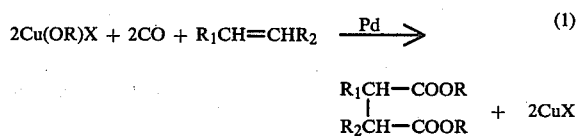

$$2Cu(OR)X + 2CO + R_1CH=CHR_2 \xrightarrow{Pd} \begin{array}{c} R_1CH-COOR \\ | \\ R_2CH-COOR \end{array} + 2CuX \qquad (1)$$

wherein symbols R and x have the meaning already given previously, while $R_1$ and $R_2$, either equal to or different from each other, may represent, as already indicated, alkyl groups having up to 6 carbon atoms, aryl, alkylaryl or arylalkyl groups having up to 8 carbon atoms, or hydrogen atoms.

In other words, according to the process of this invention, the alkyl diesters of saturated dicarboxylic acids starting from olefinic compounds, are obtained by reaction with carbon monoxide and compounds of copper (II) having the above defined formula Cu(OR)X, in the presence of palladium catalysts.

The reaction is preferably conducted in an inert solvent medium, at a temperature comprised between about 20° C. and 200° C.

As catalysts of Pd there may be used Pd salts soluble in the reaction medium used, or there may be used mixtures thereof, e.g. halides, sulphate, nitrate, acetylacetonate, acetate, etc.; but preferably there is used Pd acetylacetonate. Alternatively, there may also be used metal Pd or zerovalent Pd-complexes, well known to the skilled in the art, such as for instance palladium supported on coal or palladium complexes with ligands such as phosphines, dibenzylideneacetone, etc.

The molar ratio of the palladium to the copper (II) compound of formula Cu(OR)X, as previously defined, is preferably comprised between 0.0001 and 0.1 mols of Pd per mole of copper compound. Different ratios are likewise compatible without being, however, necessary.

The substantially anhydrous insert reaction medium is preferably constituted by monofunctional alcohols of the formula R″OH, wherein R″ represents an alkyl group having up to 8 carbon atoms, or it may consist of aliphatic or aromatic hydrocarbons or of monoethers of ethylene glycol referred to also as 2-alkoxyethylene alcohols) of the formula: $HOCH_2CH_2OR′$, wherein R′ has the meaning already given to it. Mixtures of said insert solvents may also be used.

Other insert solvents may be: benzene, acetone, ethylacetate, tetrahydrofuran, etc.

The carbon monoxide CO, either in the presence or absence of $H_2$, that is, it is possible to use synthesis gases, is fed under a partial pressure comprised between about 1 and 100 about absolute atmospheres, but is preferably comprised between 10 and 100 atmospheres, about.

The use of the carbon monoxide CO, when desired, is compatible with other inert gases.

The molar ratio between the carbon monoxide and the olefinic substrate takes different values, depending on the nature of the olefin, which may be either in the physical state of a liquid or of a gas.

Operational values of such molar ratio are practically comprised between 0.2 and 100 mols of CO per mol of olefin.

The usable reaction temperature ranges from about 20° C. to about 200° C., but preferably is comprised between about 50° C. and 120° C.

The reaction times may vary according to the temperature and pressure used as well as to the other possible varying parameters (nature of the olefin, etc.), within a wide range.

The yields in dialkyl esters according to reaction (1) of this process are practically quantitative with respect to the mols of CO fed in, and of cupric compound present, while the Pd acts exclusively as a catalyst.

The above mentioned circumstance is quite indicative of the selective course followed by the reaction.

The separation of the reaction product from the solvent and from the catalyst may be conveniently achieved by distillation according to essentially conventional methods.

As previously stated, the saturated dicarboxylic acid corresponding to the diester thereof can easily be obtained by hydrolysis reaction, also according to conventional methods.

The distillation residue, containing the CuX salt (see reaction 1) and the catalyst, may be used for further reaction cycles, after regeneration of the cupric compound Cu(OR)X, according to the known techniques: for instance, by oxidation with air and/or oxygen in an ROH alcohol medium and in a monoether $HOCH_2CH_2OR′$, wherein R, R′ and X have the meanings already repeatedly indicated herein above.

The Cu(OR)X compound may also be obtained, according to another known method, in the form of a complex with organic ligands, such as for instance pyridine and picoline, and may be used as such in the reaction according to the present process, without any hindrance.

The present invention, thanks to the mild operational conditions, foreseen for its achievement, proves to be particularly convenient.

Other advantages may be recognized in the selectivity of the reaction with respect to the desired products and in the reasonable reduction of the operational hazards connected with possible explosion phenomena, in this specific case excluded because of the absence of CO+O₂ mixtures.

Moreover, it is of particular interest that it is possible to use the CO mixtures with hydrogen, such as they are present in the production of the synthesis gases, without thereby reducing the effectiveness of the process.

When solvents of the formula HOCH₂—CH₂—OR' are used, in which R' has the known meaning, it is possible to effect the oxidation of the copper (I) CuX halide to the state of higher valency (II)

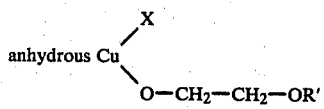

in the same reaction medium in which there is conducted the carbonylation reaction, according to this invention. In fact, the H₂O that is thus formed may be continuously removed by azeotropical distillation (X and R' having the meanings already given to them).

SPECIFIC DESCRIPTION OF THE INVENTION

The present invention will now be described in greater detail in the following examples, given for mere illustrative purposes within the scope of the invention.

EXAMPLE 1

Into a 1 liter stainless steel autoclave there were loaded:

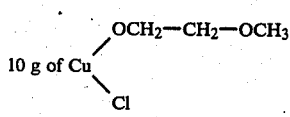

0.55 g of Pd (acetylacetonate)₂;
100 cc of anhydrous methylcellosolve.
The autoclave was then pressurized with 40 atmospheres of ethylene and with 10 atmospheres of carbon monoxide.

The autoclave was then heated up to a temperature of 80° C. and maintained at said temperature for 6 hours.

At the end of said period, the autoclave was de-pressurized and the liquid was analysed by liquid gas-chromatography (LGC). This analysis showed that there had formed 5 g of succinic acid ester.

EXAMPLE 2

Into 1 liter stainless steel autoclave, there were loaded:

40 g of Cu

0.55 g of Pd (acetylacetonate)₂;
150 cc of anhydrous methylcellosolve.
The autoclave was then pressurized with 60 atmospheres of ethylene and with 15 atmospheres of carbon monoxide. The autoclave was then heated up to a temperature of 60° C. and maintained at this temperature for 8 hours. At the end of said period the autoclave was de-pressurized and the liquid was submitted to LGC analysis. This latter showed that there had formed 18 grams of succinic acid ester.

EXAMPLE 3

Into a 2 liter autoclave, the following mixture was loaded:

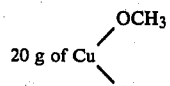

1 g of a 5% Pd/C (produced by Engelhard, Chemical Division);
20 cc of 1-hexene;
375 cc of toluene.
The autoclave was pressurized at 50 atmospheres with carbon monoxide and was then heated up to a temperature of 120° C. After 4 hours, the autoclave was discharged and there were found 7 grams of the ester of butylsuccinic acid in the liquid residue when submitted to LGC analysis.

EXAMPLE 4

A 2 liter autoclave was loaded with the following mixture:

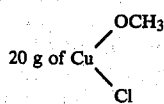

0.5 g of Pd/Kieselgur at 10% (produced by FLUKE AG, Buchs SG.);
20 cc of 1-hexene;
300 cc of toluene.
The autoclave was then pressurized up to 80 atmospheres and heated to 120° C. After 5 hours, the autoclave was discharged and, by means of LGC analysis, there were found in the residual liquid 4 grams of the ester of butylsuccinic acid.

EXAMPLE 5

A 2 liter autoclave was loaded with the following mixture:

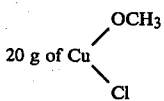

Pd/C at 5% (produced by Engelhard, Chemical Division);
25 cc of propylene;
350 cc of toluene.
The autoclave was then pressurized to 75 atmospheres with carbon monoxide and was then heated up to 120° C.

After 4 hours, the autoclave was discharged and, by means of LGC analysis, there were found in the residual liquid 6 grams of the dimethylester of methylsuccinic acid.

EXAMPLE 6

A 2 liter autoclave was loaded with the following mixture:

Pd/C at 5% (produced by Engelhard, Chemical Division);
20 cc of 1-butene;
360 cc of toluene.

The autoclave was then pressurized up to 70 atmospheres with CO, and was then heated up to a temperature of 120° C. for 4 hours. At the end of this period, the pressure was released, the liquid gathered and analysed by LGC analysis. Thereby were found 6 grams of the methyl diester of ethyl-succinic acid.

We claim:

1. A process for the preparation of alkyl diesters of saturated dicarboxylic acids, which comprises reacting an unsaturated olefinic compound having formula (II):

$$R_1CH=CHR_2 \qquad (II)$$

in which $R_1$ and $R_2$, either equal to or different from each other, are selected from the group consisting of hydrogen atoms, alkyl groups having up to 6 carbon atoms, and an aryl-alkylaryl-and arylalkyl groups having up to 8 carbon atoms, with a copper (II) compound having the formula; Cu(OR)X in which R represents a group selected from the group consisting of alkyl radical having from 1 to 8 carbon atoms and alkoxyethyl radicals —$CH_2$—$CH_2$—OR' wherein R' represents an alkyl radical having up to 6 carbon atoms, and wherein X represents chlorine or bromine, and with carbon monoxide in the presence of at least a catalyst selected from the group consisting of palladium salts, zerovalent palladium compounds and metal palladium, at a temperature comprised between about 20° C. and 200° C.

2. A process according to claim 1, characterized in that the copper (II) compound Cu(OR)X is the one in which R is an alkyl radical having up to 4 carbon atoms, while X represents a chlorine atom.

3. A process according to claim 1, characterized in that the catalyst is selected from the group consisting of Pd halides, nitrate, acetate, sulphate, acetylacetonate, Pd on coal, Pd complexes with phosphines and Pd complexes with dibenzylideneacetone.

4. A process according to claim 1, characterized in that the catalyst consists of Pd (acetylacetonate)$_2$.

5. A process according to claim 1, characterized in that the molar ratio of Pd to the copper compound Cu(OR)X is comprised between 0.0001 mol and 0.1 mol of Pd per mol of copper compound.

6. A process according to claim 1, characterized in that said process is conducted in a substantially anhydrous inert medium selected from the group consisting of monofunctional R"OH alcohols, monoethers of ethylene glycol of the formula:

$$HOCH_2CH_2OR',$$

wherein R' is an alkyl having up to 8 carbon atoms, and R' is an alkyl having up to 6 carbon atoms, aliphatic and aromatic hydrocarbons, benzene, acetone, ethylacetate, tetrahydrofurane, methylcellosolve and mixtures thereof.

7. A process according to claim 1, characterized in that said process is conducted at CO partial pressures comprised between 1 and 100 absolute atmospheres.

8. A process according to claim 1, characterized in that the carbon monoxide is fed in admixture with $H_2$ coming from the industrial preparation of the synthesis gas.

9. A process according to claim 1, characterized in that the molar ratio between the carbon monoxide and the olefinic reactant is comprised between 0.2 mols and 100 mols about of CO per mol of olefin.

10. A process according to claim 1, characterized in that said process is conducted at a temperature comprised between 20° C. and 200° C.

11. A process according to claim 1 characterized in that the preparation of the copper compound:

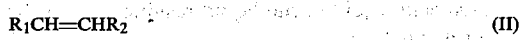

wherein X represents chlorine or bromine and R' represents an alkyl radical having up to 6 carbon atoms is carried out in the same reaction medium in which occurs the carbonylation reaction, when carried out in the presence of monoethers of ethylene glycol as solvents.

* * * * *